United States Patent
Geffard et al.

(10) Patent No.: US 11,389,417 B2
(45) Date of Patent: Jul. 19, 2022

(54) ACTIVE INGREDIENT CONSISTING OF A MIXTURE OF POLYLYSINE COMPOUNDS AND USE IN THE PREVENTION OF STROKES AND THE TREATMENT OF THE POST-STROKE INFLAMMATORY PHASE

(71) Applicant: POLYNEUROS, Villenave d'Ornon (FR)

(72) Inventors: Michel Geffard, Talence (FR); Arturo Mangas Martin, Martignas-sur-Jalles (FR); Laëtitia Vidal, Ambares et Lagrave (FR)

(73) Assignee: POLYNEUROS, Villenave d'Ornon (FR)

( * ) Notice: Subject to any disclaimer, the term of this patent is extended or adjusted under 35 U.S.C. 154(b) by 243 days.

(21) Appl. No.: 16/613,963

(22) PCT Filed: May 14, 2018

(86) PCT No.: PCT/EP2018/062309
§ 371 (c)(1),
(2) Date: Nov. 15, 2019

(87) PCT Pub. No.: WO2018/210710
PCT Pub. Date: Nov. 22, 2018

(65) Prior Publication Data
US 2021/0330623 A1    Oct. 28, 2021

(30) Foreign Application Priority Data
May 16, 2017   (FR) ...................................... 1770496

(51) Int. Cl.
| | | |
|---|---|---|
| *A61K 31/198* | (2006.01) | |
| *A61P 9/10* | (2006.01) | |
| *A61K 9/00* | (2006.01) | |
| *A61K 9/19* | (2006.01) | |
| *A61K 31/355* | (2006.01) | |

(52) U.S. Cl.
CPC ............ *A61K 31/198* (2013.01); *A61K 9/006* (2013.01); *A61K 9/0019* (2013.01); *A61K 9/0053* (2013.01); *A61K 9/19* (2013.01); *A61K 31/355* (2013.01); *A61P 9/10* (2018.01)

(58) Field of Classification Search
CPC .................................................... A61K 31/198
See application file for complete search history.

(56) References Cited

U.S. PATENT DOCUMENTS

| | | | | |
|---|---|---|---|---|
| 7,799,782 | B2 * | 9/2010 | Munson ................... | A61P 35/00 514/234.5 |
| 2009/0325856 | A1 * | 12/2009 | Geffard ................ | A61K 31/201 514/1.1 |

FOREIGN PATENT DOCUMENTS

| | | |
|---|---|---|
| EP | 1870095 A1 | 12/2007 |
| WO | WO2008035001 A2 | 3/2008 |

OTHER PUBLICATIONS

Arturo et al, "Gemst: a taylor-made combination that reverts neuroanatomical changes in stroke", European Journal of Histochemistry, (May 3, 2017), pp. 102-111, vol. 61, No. 2.
Arturo et al., "A New Drug Candidate (GEMSP) for Multiple Sclerosis", Current Medicinal Chemistry, (2009), pp. 3203-3214, vol. 16, No. 25.

* cited by examiner

*Primary Examiner* — Rei Tsang Shiao
(74) *Attorney, Agent, or Firm* — Greer, Burns & Crain, Ltd.

(57) ABSTRACT

The invention relates to an active ingredient consisting of several polylysine compounds, said polylysine compounds consisting of at least one small molecule conjugated to a polylysine, said active ingredient comprising at least the following polylysine compounds:
  Coenzyme Q10-Polylysine
  Retinoic Acid-Polylysine
  Cysteine-Polylysine
  Taurine-Polylysine
  Glutathione-Polylysine,
for use in humans or animals, to prevent strokes and/or treat the inflammatory phase following a stroke.

15 Claims, No Drawings

ACTIVE INGREDIENT CONSISTING OF A MIXTURE OF POLYLYSINE COMPOUNDS AND USE IN THE PREVENTION OF STROKES AND THE TREATMENT OF THE POST-STROKE INFLAMMATORY PHASE

CROSS-REFERENCE TO RELATED APPLICATIONS

This application is the U.S. National phase application corresponding to PCT/EP2018/062309 which was assigned an international filing date of May 14, 2018 and associated with publication WO 2018/210710 and which claims priority to French Patent Application FR 1770496 filed on May 16, 2017, the disclosures of which are expressly incorporated herein by reference.

TECHNICAL FIELD

This invention relates to preventing the risk of strokes in humans or animals and to treating the inflammatory phase following a stroke.

BACKGROUND

A stroke is defined by the World Health Organization as the consequence of a sudden interruption of cerebral blood flow. Approximately 80-85% of strokes are of ischemic origin and 15-20% of hemorrhagic origin.

The main global risk factors are tobacco use, high blood pressure, physical inactivity, unhealthy diet, obesity, diabetes, a high level of blood lipids, irresponsible consumption of alcohol, aging, low level of education about these topics, as well as genetic and psychological factors.

Cardiovascular disease is the leading cause of death worldwide, i.e. almost 17 million deaths a year according to a report by the WHO (S. Mendis, Puska P., B. Norrving, World Health Organization, World Heart Federation, World Stroke Organization, 2011. *Global Atlas on Cardiovascular Disease Prevention and Control*. World Health Organization: World Heart Federation: World Stroke Organization, Geneva), a major share of which is due to strokes since this is the second biggest cause of mortality in the cardiovascular disease category. In addition, strokes are the leading cause of adult acquired disability, the second biggest cause of dementia, and the third biggest cause of death in France.

There is currently no specific therapy for strokes. The only effective treatment is an intravenous injection of a tissue plasminogen activator (tPA). However, tPA has a very short therapeutic window and is limited to a few hours after a stroke, even in the case of ischemic strokes. During the cell processes initiated during a stroke, tPA has no inflammatory, edematous and immune effect, and cannot be used in the case of hemorrhagic strokes. The search for new therapeutic, preventive and healing solutions is therefore a major public health issue.

SUMMARY

This invention falls within this context and aims to provide a therapeutic solution to prevent and fight against the consequences of strokes that is more effective and applicable than the current rare and unsuitable treatments.

To this end, the invention relates to an active ingredient consisting of several polylysine compounds, said polylysine compounds consisting of at least one small molecule conjugated to a polylysine, said active ingredient comprising at least the following polylysine compounds:
Coenzyme Q10-Polylysine,
Retinoic Acid-Polylysine,
Cysteine-Polylysine,
Taurine-Polylysine, and
Glutathione-Polylysine.

According to the invention, this active ingredient is effective in humans and animals to prevent strokes and/or treat the inflammatory phase following a stroke.

Advantageously, it makes it possible in particular to:
control the free radical, immunological and degenerative mechanisms of strokes and,
optimize the environment for implanting repair cells such as embryonic, mesenchymal, and totipotent stem cells.

The active ingredient according to the invention has in particular an anti-inflammatory effect on lesions located in the brain, on cholesterol deposition, and on clot formation. It limits the release of free radicals and glutamate so as to control the immune system and protect the brain, and limits the release of pro-inflammatory cytokines that release microglia and hence makes it possible to "clean" non-irrigated arterial tissue.

The invention also relates to a composition for use in preventing strokes and/or treating the inflammatory phase following a stroke, comprising at least 7 mg by weight of an active ingredient in the compressed dosage form according to the invention.

Other features and advantages will become apparent from the detailed description of the invention which follows.

Definitions

"Small molecule conjugated to a polylysine" or "small molecule grafted to a polylysine" in the sense of the invention means a molecule bound to the polylysine by covalent or noncovalent binding (especially hydrogen or ionic Van der Waals bonds). Polylysine is a macromolecule of lysine units, preferably linear or branched L-lysine (poly-L-lysine), whose number (n) of subunits is preferably at least 30 lysines: n 30 lysines.

"Stroke prevention" in the sense of the invention means neutralizing or controlling the free radicals generated by the lack of oxygen to the brain before a stroke, in particular by enabling the active ingredients to be present in the brain before a stroke. The more the free radicals are neutralized in the early stages of a stroke, the more the consequences of a stroke are limited.

"Excitotoxicity phase at the time of a stroke" means immediately after reperfusion of arterial tissue (blood clot removal), which corresponds to an increase of free radicals and glutamate as a cytotoxic molecule triggering the inflammatory and apoptotic phase.

"Inflammatory and apoptotic phase following a stroke" means the activation of enzyme systems such as the NO synthesis pathway and the 2,3-indolamine dioxygenase (IDO) pathway, activation of reaction cascades, such as the caspases that initiate the following phases. This phase may last from a few days to a few weeks, depending on the severity of the stroke.

"Repair and regeneration phase following a stroke" in the sense of the invention means a phase wherein the symptoms of the neurological deficit caused by a stroke improve.

The active ingredient provides a favorable environment for cell repair and local repair of the stimulated totipotent cells that develop.

"Treatment of the inflammatory and apoptotic phase following a stroke" in the sense of the invention means reducing the brain damage caused by this phase, by reducing oxidative and nitrosative stress and the release of inflammatory cytokines, which makes it possible to "clean" cells during apoptosis and necrosis.

"Active ingredient" in the sense of the invention means a therapeutic active ingredient, i.e. a set of molecules having a therapeutic effect and present in a very small proportion relative to the excipients.

DETAILED DESCRIPTION OF THE INVENTION

The invention therefore relates to an active ingredient consisting of several polylysine compounds, said polylysine compounds consisting of at least one small molecule conjugated to a polylysine for use in humans or animals to prevent strokes and/or treat the inflammatory phase following a stroke. The active ingredient according to the invention can be used to protect from the harmful effects of a stroke.

The effective active ingredient according to the invention comprises at least the following polylysine compounds:
  Coenzyme Q10-Polylysine,
  Retinoic Acid-Polylysine,
  Cysteine-Polylysine,
  Taurine-Polylysine, and
  Glutathione-Polylysine.

The active ingredient according to the invention can be used in particular to reduce inflammation in the arteries to prevent strokes in patients at risk and/or to treat the inflammatory phase following a stroke. This is because it is able to act as an inhibitor of oxidative stress thanks to the contribution of antioxidants such as vitamins.

It can also be used to reduce destruction of viable neurons by immune cells during treatment in the inflammatory and apoptotic phase following a stroke. This is because it is able to act on the balance of neurotoxic/neuroprotective molecules in the IDO pathway (for example, 3-hydroxyanthranilic acid/kynurenic acid), microglial, glial, and lymphocytic cells involved in the immune system.

Regular vitamin intake in patients at risk decreases the prevalence of strokes. The earlier a stroke is treated by vitamin intake, the more the consequences of a stroke, as well as brain destruction and the volume of lesions in the ischemic area, are reduced.

Coenzyme Q10 in particular has a neuroprotective effect thanks to its antioxidant power. Retinoic acid in particular acts as an anti-apoptotic and antioxidant agent.

Cysteine is particularly able to protect nerve cells from the toxicity of zinc released by nerve cells by chelating the zinc or converting it into an intermediate product in the carboxylic acid cycle.

Taurine is particularly able to protect against excitotoxicity. It has a neuroprotective effect against the apoptosis caused by endoplasmic reticulum-related stress. It is also able to preserve mitochondrial function and prevent cell death related to the mitochondrial pathway of apoptosis. It also has the effect of maintaining the homeostasis of neuronal control and of preventing neuron cell death.

Glutathione plays an important role in antioxidant defense, nutrient metabolism and in the regulation of cellular events.

These different constituents of the active ingredient according to the invention act together and synergistically to achieve an effect in preventing strokes and in treating the inflammatory phase following a stroke. This is because the active ingredient according to the invention is able to generate the environmental conditions necessary for repair, for reducing neurotoxic molecules, and for reducing inflammation. This enables better control of the ischemic area wherein apoptotic neuron death has occurred.

The combination of the specific polylysine compounds constituting the active ingredient (polycomplex) according to the invention makes it possible to repair brain damage by reducing oxidative and nitrosative stress and to reduce the release of inflammatory cytokines, which makes it possible to "clean" cells during apoptosis and necrosis. The active ingredient according to the invention thus regulates the immune activation, decreases harmful effects by reducing the markers IBA1 (macrophage), CD45 (pan-leucocyte), CD11b (activated microglia), and GFAP (astrogliosis). Molecules in the IDO pathway, such as 3-hydroxyanthranilic acid and kynurenic acid, are overexpressed in the case of a stroke (see results on the animal model used in the experimental part, which consists of interrupting the blood flow for about 1 hour, followed by reperfusion of the brain tissue), and using the active ingredient according to the invention makes it possible to modulate this metabolic pathway. Moreover, the polylysine compounds constituting the active ingredient according to the invention pass directly through the sublingual vascular wall and are thus distributed by the blood to the lesions in order to neutralize the radical species and thus avoid endogenous protein modifications, and hence neuron death.

In addition, these various molecules are rendered active by being conjugated to polylysine. This is because polylysine is an alpha-polylysine cationic polypeptide, whose characteristics of linearity, non-immunogenicity, and random coil secondary structure give it the property of rendering a small molecule active once it is bound to the polylysine.

The preventive effect of the active ingredient according to the invention can be either before a person at risk has a first stroke, or after a stroke to prevent another stroke.

In addition to the following polylysine compounds:
  Coenzyme Q10-Polylysine,
  Retinoic Acid-Polylysine,
  Cysteine-Polylysine,
  Taurine-Polylysine, and
  Glutathione-Polylysine,
the active ingredient according to the invention may consist of other polylysine compounds. Preferably, the active ingredient according to the invention also comprises at least one of the following polylysine compounds:
  α-Tocopherol-Polylysine
  Ascorbic Acid-Polylysine
  Methionine-Polylysine.

It may therefore include at least one of these compounds, or at least two or all three. It can also include other compounds.

The α-Tocopherol has a significant antioxidant effect. This effect is increased in the presence of ascorbic acid.

In addition, ascorbic acid as such is particularly able to protect neurons from excitotoxicity and prevent glutamate-induced cell damage and cell death.

Methionine acts as an endogenous antioxidant defense system in cells and is also a precursor of glutathione.

In combination with the other specific compounds of the active ingredient according to the invention, they act in synergy to achieve an effect in preventing strokes and in treating the inflammatory phase following a stroke.

In one embodiment, the active ingredient according to the invention consists exclusively of the following polylysine compounds:
Coenzyme Q10-Polylysine
Retinoic Acid-Polylysine
Cysteine-Polylysine
Taurine-Polylysine
Glutathione-Polylysine In another preferred embodiment, the active ingredient according to the invention consists exclusively of the following polylysine compounds:
Coenzyme Q10-Polylysine
Retinoic Acid-Polylysine
Cysteine-Polylysine
Taurine-Polylysine
Glutathione-Polylysine
α-Tocopherol-Polylysine
Ascorbic Acid-Polylysine
Methionine-Polylysine.

In the active ingredient according to the invention, regardless of its composition, the polylysine constituting the polylysine compounds is preferably poly-L-lysine. Biologically active systems very generally consist of amino acids in an L-configuration, called "natural".

Each of the small molecules constituting the polylysine compounds in the active ingredient is present in concentrations preferably ranging between $1 \times 10^{-4}$ and $1 \times 10^{-3}$ M. In one suitable embodiment, all the polylysine compounds have the same concentration, or an almost identical concentration, of small molecules to obtain the best therapeutic effect.

The active ingredient according to the invention can be obtained by a method comprising the following steps:
Synthesis of polylysine compounds
Mixing of polylysine compounds.

The synthesis of polylysine compounds can be carried out by grafting the small molecules to polylysine, according to the knowledge of those skilled in the art.

The retinoic acid-polylysine compound can for example be obtained according to the method described below:
retinoic acid (retinoyl) is activated by ethyl chloroformate (ECF), which reacts as a coupling agent by activating the carboxylic acid in the vitamin,
the activation is facilitated by adding a polar solvent, the intermediate product (retinoyl-ECF) reacts on the epsilon amine group of the lysyl residue of the polylysine by forming an amide bond,
the retinoyl-polylysine compound is then purified, ideally by tangential ultrafiltration, and then lyophilized if necessary,
the retinoic acid is then grafted to the polylysine by a covalent bond.

The coenzyme Q10-polylysine and α-tocopherol-polylysine compounds can be manufactured in the same way.

The ascorbic acid-polylysine compound can for example be obtained according to the method described below:
ascorbic acid (ascorbyl) is activated by carbodiimide (EDC), which reacts as a coupling agent by activating the carboxylic acid in the vitamin,
this activation is facilitated by adding a catalyst, the intermediate product (ascorbyl-EDC) reacts on the epsilon amine group of the lysyl residue of the polylysine by forming an amide bond,
the ascorbyl-EDC-polylysine compound is then purified, ideally by tangential ultrafiltration, and then lyophilized if necessary,
the ascorbic acid is then grafted to the polylysine by a covalent bond.

The cysteine-polylysine compound may for example be obtained according to the method described below:
cysteine is activated by glutaraldehyde (G), which reacts as a coupling agent by activating the amine of the amino acid,
the intermediate (cysteine-G) reacts on the epsilon amino group of the lysyl residue by forming an amide bond,
the cysteine-G-polylysine compound is then purified, ideally by tangential ultrafiltration, and then lyophilized if necessary,
the cysteine is then grafted to the polylysine by a covalent bond.

The methionine-polylysine, taurine-polylysine and glutathione-polylysine compounds can be manufactured in the same way.

Polylysine compounds are then mixed to manufacture the active ingredient according to the invention. Preferably, the mixture is produced by implementing a method comprising the following steps:
recovery of the indicated amounts of each polylysine compound in liquid form,
calculation for each polylysine compound of the concentration of small molecules, using a given volume to be taken relative to the desired final concentration and final volume of the mixture,
before removal, the polylysine compounds are stirred manually or mechanically,
the polylysine compounds in the liquid phase are then mixed after pipetting with magnetic stirring,
emulsification of the liquid mixture is carried out at temperatures between 18° C. and 22° C., with vigorous mechanical stirring at between 60 and 400 revolutions/min,
the resulting mixture is frozen and then lyophilized to obtain a powder, or the mixture obtained is used in liquid form.

The active ingredient according to the invention may be in dry form (preferably lyophilized) or in liquid form (solution).

Advantageously, the active ingredient according to the invention is very effective while also having no adverse side-effects. Indeed, animal experiments have confirmed the absence of toxicity and undesirable side-effects.

For its use in stroke prevention, the active ingredient according to the invention is preferably used at between 5 and 15 mg per day, in particular at between 7 and 10 mg, in dry form.

The target people for prevention and for taking the active ingredient according to the invention in this context are people at risk of a stroke, i.e. especially people with hypercholesterolemia, hypertension, people at risk who have already had a stroke, sedentary people, combined with consuming alcohol, tobacco, and other factors.

For its use in treating the inflammatory phase following a stroke, the active ingredient according to the invention is used at between 5 and 15 mg per day, preferably at between 7 and 10 mg, in dry form or in injectable form, depending on the severity of the stroke.

The target people for this treatment and for taking the active ingredient according to the invention in this context are people who have had a stroke, during a period preferably ranging from immediately after the stroke to 2 weeks afterwards, and continuously for an indefinite period, which is the life-threatening period.

The active ingredients and compositions according to the invention are particularly effective in the context of late-phase treatment of strokes.

The active ingredient according to the invention can be combined with other therapies, such as for example plasminogen and/or other new therapies, the active ingredient according to the invention being compatible with other active ingredients and being non-immunogenic. Advantageously, it can be used over long periods of time, which is an advantage because there are no undesirable side-effects, which is important in the case of strokes because their prevalence increases with age and with a first episode of stroke.

The active ingredient is very preferably used in a composition.

The invention therefore also relates to a composition for use in humans or animals to prevent strokes and/or to treat the inflammatory phase following a stroke, comprising at least 7 mg by weight of an active ingredient in the compressed dosage form according to the invention. The composition may be in solid form, in particular in dry form. It may be for example a tablet to be swallowed, a sublingual tablet, a gastro-resistant capsule, a powder, a dermal patch, or a suppository. The composition in dry form comprises at least one excipient, such as for example an atomization medium such as maltodextrin, for example, or microcrystalline cellulose or magnesium stearate or polyethylene glycol.

When the composition is in dry form, the active ingredient according to the invention is preferably present at between 5 and 15 mg per 100 mg of composition, and even more preferably at between 7 and 10 mg per 100 mg of composition.

The composition can be in liquid form. In particular, it can be in the form of an oral solution or suspension or injectable solution. It may act as a major excipient, for example sodium chloride and purified water, or sorbitol and purified water or saccharin and purified water. When the composition is in liquid form, the active ingredient according to the invention is preferably present at between 5 and 15 mg per ml of composition, and even more preferably at between 7 and 10 mg per ml of composition.

The invention is now illustrated by examples and test results demonstrating the efficacy of the active ingredient.

Examples of active ingredients (polycomplexes) according to the invention

Method for Producing Polycomplexes

The polycomplexes are obtained according to the following method:
- recovery of the indicated amounts of each polylysine compound in liquid form;
- obtaining for each polylysine compound with a calculation of its concentration of small molecules, a given volume to be taken relative to the desired final concentration and final volume for the polycomplex, i.e. from 1000 to 10000 ml;
- before removal, the polylysine compounds are stirred manually or mechanically;
- the polylysine compounds in the liquid phase are then mixed after pipetting with magnetic stirring;
- emulsification of the liquid mixture is carried out at temperatures between 18° C. and 22° C., by vigorous mechanical stirring at 100 revolutions/min;
- the emulsion from the mixture is also homogenized by sonification;
- the mixture obtained is frozen and then lyophilized to obtain a powder.

Example 1: Example of Polycomplex 1 (Active Ingredient) According to the Invention

| Poly-L-Lysine compounds | Final concentration (in mol/L) In small grafted molecules |
| --- | --- |
| COENZYMEQ10-Poly-L-Lysine | $2 \times 10^{-4}$ |
| RETINOIC ACID-Poly-L-Lysine | $2 \times 10^{-4}$ |
| CYSTEINE-Poly-L-Lysine | $2 \times 10^{-4}$ |
| TAURINE-Poly-L-Lysine | $2 \times 10^{-4}$ |
| GLUTATHIONE-Poly-L-Lysine | $2 \times 10^{-4}$ |

Weight: 4.7 mg per tablet

Example 2: Example of Polycomplex 2 (Active Ingredient) According to the Invention

| Poly-L-Lysine compounds | Final concentration (in mol/L) In small grafted molecules |
| --- | --- |
| COENZYMEQ10-Poly-L-Lysine | $2 \times 10^{-4}$ |
| RETINOIC ACID-Poly-L-Lysine | $2 \times 10^{-4}$ |
| CYSTEINE-Poly-L-Lysine | $2 \times 10^{-4}$ |
| TAURINE-Poly-L-Lysine | $2 \times 10^{-4}$ |
| GLUTATHIONE-Poly-L-Lysine | $2 \times 10^{-4}$ |
| TOCOPHEROL-Poly-L-Lysine | $2 \times 10^{-4}$ |
| ASCORBIC ACID-Poly-L-Lysine | $2 \times 10^{-4}$ |
| METHIONINE-Poly-L-Lysine | $2 \times 10^{-4}$ |

Weight: 7.5 mg per tablet

Example 3: Example of Polycomplex 3 (Active Ingredient) from the Prior Art

| Poly-L-Lysine compounds | Final concentration (in mol/L) In small grafted molecules |
| --- | --- |
| COENZYMEQ10-Poly-L-Lysine | $4 \times 10^{-4}$ |
| RETINOIC ACID-Poly-L-Lysine | $4 \times 10^{-4}$ |
| TOCOPHEROL-Poly-L-Lysine | $4 \times 10^{-4}$ |
| ASCORBIC ACID-Poly-L-Lysine | $4 \times 10^{-4}$ |

Weight: 7.5 mg per tablet

Example 4: Example of Polycomplex 4 (Active Ingredient) from the Prior Art

| Poly-L-Lysine compounds | Final concentration (in mol/L) In small grafted molecules |
| --- | --- |
| CYSTEINE-Poly-L-Lysine | $4 \times 10^{-4}$ |
| TAURINE-Poly-L-Lysine | $4 \times 10^{-4}$ |
| GLUTATHIONE-Poly-L-Lysine | $4 \times 10^{-4}$ |
| METHIONINE-Poly-L-Lysine | $4 \times 10^{-4}$ |

Weight: 7.5 mg per tablet

Example 5: Example of a Composition Comprising Polycomplex 2 with Excipients in Solid Form The composition in example 5 for a therapeutic unit (1 tablet) is as follows:

| Components | Content (%) |
|---|---|
| Mannitol (for direct compression) | 56.5 |
| Pregelatinized starch | 14 |
| Microcrystalline cellulose | 10 |
| PEG | 5 |
| PVP K30 | 2 |
| Talc | 2 |
| Magnesium Stearate | 1 |
| Amorphous silica | 1 |
| Lévilite | 1 |
| Total excipients | 92.5 |
| Active ingredient according to the invention: example 2 | 7.5 |
| Total | 100 |

The composition according to the invention is present in the form of a 100 mg sublingual tablet.

The powder containing the active ingredients and the excipients is pressed to form the sublingual tablet so that it can dissolve in 3 to 10 minutes.

The dosage for this tablet prescribed alone is 2 tablets 3 times a day, two days out of three, i.e. 90 mg of antioxidants and free radical scavengers per month.

Example 6: Example of Composition Comprising Polycomplex 2 with Excipients in Oral Solution The composition in example 6 for a therapeutic unit (100 ml) is as follows:

| Components | Content (%) |
|---|---|
| Purified Water | 74 |
| Saccharin | 5 |
| Sorbitol | 4 |
| Aroma | 2 |
| Total excipients | 85 |
| Active ingredient according to the invention: example 2 | 15 |
| Total | 100 |

Tests Demonstrating the Efficacy of the Invention

Trials were performed on a stroke model in rats, which consisted of interrupting blood flow for approximately one hour followed by reperfusion of brain tissue (Mangas A., Yajeya J., Gonzalez N., Ruiz I., Geffard M., Coveñas R., 3-hydroxi-anthranilic acid *Eur J Histochem* 2016; 60: 2709; Mangas A., Yajeya J., González N., Ruiz I., Duleu S., Geffard M., Coveñas R., Overexpression of kynurenic acid in stroke: an endogenous neuroprotector? *Ann Anat* 2017; 211: 33-8. UluçK., Miranpuri A., Kujoth G. C., Aktüre E., Başkaya M. K., Focal cerebral ischemia model by endovascular suture occlusion of the middle cerebral artery in the rat *J Vis Exp*. 2011 Feb. 5; (48). pii: 1978)

The operating protocol is described hereafter.

A nylon filament with a silicone tip was inserted into the internal carotid artery up to the median artery, interrupting the blood flow for one hour. After one hour, the filament was removed and the blood flow was restored. During the resuscitation phase, the active ingredient according to the invention was injected.

The aim of the trials was to demonstrate that animals treated after reperfusion for 21 days show a reversal of the harmful effects caused by being deprived of blood flow.

The results obtained are shown in the table below:

| Marker | Positive Control I/C | | Active ingredient according to the invention (example 2) I/C | | Active ingredients from the prior art (examples 3 and 4) I/C | | Control Negative |
|---|---|---|---|---|---|---|---|
| IBA1 | +++ | + | + | + | ++ | + | + |
| GFAP | +++ | + | + | + | ++ | + | + |
| CD45 | +++ | − | − | − | ++ | − | − |
| CD11b | +++ | − | − | − | ++ | − | − |
| KYNA | +++ | − | − | − | AQNE | − | − |
| 3-HAA | +++ | − | − | − | AQNE | − | − |

AQNE: Quantitative analysis not assessed but positive immunoreactivity;
I/C: ipsilateral side/contralateral side;
+++: high density;
++: moderate density;
+: low density;
−: absence of immunoreactivity
(test carried out according to the method described in Mangas A., Yajeya J., González N., Ruiz I., Geffard M., Coveñas R., 3-hydroxi-anthranilic acid is early expressed in stroke. *Eur J Histochem* 2016; 60: 2709. Mangas A., Yajeya J., González N., Ruiz I., Duleu S., Geffard M., Coveñas R., Overexpression of kynurenic acid in stroke: an endogenous neuroprotector? *Ann Anat* 2017; 211: 33-8).

It was found that animals not treated with example 2 (invention) have a damaged region (striatum and or cortex), which is characterized by overexpression of IBA1 and GFAP markers in the lesion region compared to the contralateral hemisphere. This is not the case with the animals in the negative control group of the model, as well as the animals treated with the invention.

The presence of activated microglia (assessed with the CD11b marker) and leukocyte infiltration (assessed with the CD45 pan-leucocytic marker) is notable only in the lesion area of the 21-day vehicle-treated animals and those treated with examples 3 and 4; healthy animals (negative control) and animals treated with the active ingredient (example 2) do not have this infiltration. It should be noted that in the same damaged region, there is a co-existence of metabolites in the IDO pathway (3-hydroxyanthranilic acid and kynurenic acid) in the astrocytes. It is known that 3-hydroxyanthranilic acid has neurotoxic effects and that kynurenic acid has neuroprotective effects. Overexpression of these 2 molecules is due to the activation of the IDO pathway in the present stroke model (Mangas et al., 2016, 2017). This overexpression is inhibited after treatment with the active ingredient (example 2) according to the invention. Thus, the active ingredient according to the invention restores the pathological conditions induced by the stroke model to conditions called "normal". In addition, it makes it possible to abolish infiltration into the brain, activation of microglia, astrogliosis and to modulate the IDO pathway, at least for 3-hydroxyanthranilic acid and kynurenic acid.

The polylysine compounds constituting the active ingredient according to the invention (example 2) are thus able to neutralize the harmful effects 21 days after a stroke, in comparison with the untreated animals (positive control) and the animals treated using the prior art (examples 3 and 4).

The invention claimed is:

1. An active ingredient for treating a human or animal in the inflammatory phase following a stroke, the active ingredient consisting of several polylysine compounds, said polylysine compounds consisting of at least one small molecule conjugated to a polylysine, wherein said active ingredient is at least the following polylysine compounds:
   Coenzyme Q10-Polylysine,
   Retinoic Acid-Polylysine,
   Cysteine-Polylysine, Taurine-Polylysine, and
Glutathione-Polylysine.

2. The active ingredient of claim 1, wherein the polylysine is Poly-L-lysine.

3. The active ingredient of claim 1, wherein a concentration of each of said small molecules is between $1 \times 10^{-4}$ and $1 \times 10^{-3}$ M.

4. The active ingredient of claim 1, wherein all said polylysine compounds have the same concentration of small molecules.

5. A composition for treating the inflammatory phase following a stroke, the composition comprising at least 7 mg by weight of the active ingredient of claim 1.

6. The composition of claim 5, wherein the composition is in dry form.

7. The composition of claim 6, wherein the composition is in the form of a tablet to be swallowed, a sublingual tablet, a gastro-resistant capsule, a powder, a dermal patch, or a suppository.

8. The composition of claim 6, wherein the active ingredient is present at between 5 and 15 mg per 100 mg of the composition.

9. The composition of claim 5, wherein the composition is in liquid form.

10. The composition of claim 9, wherein the composition is in the form of an oral or injectable solution.

11. The composition of claim 9, wherein the active ingredient is present at a concentration of between 5 and 15 mg per ml of the composition.

12. A method for treating a subject in need of treatment for a stroke, the method comprising administering to the subject the composition of claim 5.

13. A method for treating artery inflammation in a subject, wherein the subject is at risk of stroke, or the subject is in the inflammatory phase following a stroke, and wherein the method comprises administering to the subject the active ingredient of claim 1.

14. A method for treating a subject, wherein the subject is in need of treatment for stroke, wherein the method comprises administering to the subject the active ingredient of claim 1, and wherein administering to the subject of the active ingredient inhibits destruction of viable neurons by immune cells of the subject during treatment in the inflammatory and apoptotic phase following a stroke.

15. The active ingredient of claim 1, wherein the active ingredient consists of:
Coenzyme Q10-Polylysine,
Retinoic Acid-Polylysine,
Cysteine-Polylysine,
Taurine-Polylysine,
Glutathione-Polylysine,
α-Tocopherol-Polylysine,
Ascorbic Acid-Polylysine, and
Methionine-Polylysine.

\* \* \* \* \*